(12) United States Patent
Gale et al.

(10) Patent No.: US 11,109,968 B2
(45) Date of Patent: Sep. 7, 2021

(54) APPARATUS AND METHODS FOR IMPROVED LOADING OF A TRANSCATHETER HEART VALVE

(71) Applicant: St. Jude Medical, Cardiology Division, Inc., St. Paul, MN (US)

(72) Inventors: Caytlin Gale, Minneapolis, MN (US); Ryan Finn, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 337 days.

(21) Appl. No.: 16/105,563

(22) Filed: Aug. 20, 2018

(65) Prior Publication Data

US 2019/0053900 A1    Feb. 21, 2019

Related U.S. Application Data

(60) Provisional application No. 62/548,120, filed on Aug. 21, 2017.

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/2427* (2013.01); *A61F 2/9524* (2020.05); *A61F 2/9525* (2020.05); *A61F 2/9526* (2020.05); *A61F 2/9522* (2020.05); *A61F 2220/0075* (2013.01); *A61F 2220/0091* (2013.01)

(58) Field of Classification Search
CPC .................. A61F 2/2436; A61F 2/2427; A61F 2002/9522; A61F 2/9522
See application file for complete search history.

(56) References Cited

U.S. PATENT DOCUMENTS

| 1,268,171 | A | * | 6/1918 | Spaulding ............. B23B 31/202 |
| | | | | 279/42 |
| 5,810,873 | A | | 9/1998 | Morales |
| 6,167,605 | B1 | * | 1/2001 | Morales ................. A61F 2/958 |
| | | | | 29/282 |
| 8,562,663 | B2 | | 10/2013 | Mearns et al. |
| 8,973,234 | B2 | | 3/2015 | Johnson et al. |

(Continued)

FOREIGN PATENT DOCUMENTS

EP    2865355 A1    4/2015

OTHER PUBLICATIONS

International Search Report including Written Opinion for PCT/US2018/047061 dated Dec. 12, 2018.

*Primary Examiner* — Katherine M Rodjom
(74) *Attorney, Agent, or Firm* — Lerner, David, Littenberg, Krumholz & Mentlik, LLP

(57) ABSTRACT

An assembly for collapsing a prosthetic heart valve includes a compression member having a plurality of arms pivotable between a first orientation in which side edges of adjacent arms are spaced apart from one another and a second orientation in which the adjacent arms contact one another. A translating member is movable along the arms to pivot the arms from the first orientation to the second orientation to collapse the prosthetic heart valve. A separation tool includes ribs defining channels sized to receive the struts of a stent of a prosthetic heart valve to keep the struts separated from one another as the prosthetic heart valve is collapsed.

11 Claims, 15 Drawing Sheets

(56) References Cited

U.S. PATENT DOCUMENTS

| | | |
|---|---|---|
| 9,192,469 B2 | 11/2015 | Mearns et al. |
| 9,414,914 B2 | 8/2016 | Duffy et al. |
| 9,414,917 B2 | 8/2016 | Young et al. |
| 2006/0025857 A1* | 2/2006 | Bergheim ............. A61F 2/2409 |
| | | 623/2.18 |
| 2007/0239271 A1 | 10/2007 | Nguyen |
| 2012/0078352 A1 | 3/2012 | Wang et al. |
| 2014/0215791 A1 | 8/2014 | Soundararajan et al. |
| 2014/0331475 A1 | 11/2014 | Duffy et al. |
| 2015/0107078 A1 | 4/2015 | Jahn et al. |
| 2016/0144158 A1* | 5/2016 | Abbate ............... A61M 31/002 |
| | | 606/199 |
| 2016/0278955 A1 | 9/2016 | Liu et al. |

\* cited by examiner

APPARATUS AND METHODS FOR IMPROVED LOADING OF A TRANSCATHETER HEART VALVE

CROSS-REFERENCE TO RELATED APPLICATIONS

The present application claims the benefit of the filing date of U.S. Provisional Patent Application No. 62/548,120 filed Aug. 21, 2017, the disclosure of which is hereby incorporated herein by reference.

BACKGROUND OF THE INVENTION

The present disclosure relates to prosthetic heart valve implantation and, more particularly, to the loading of collapsible prosthetic heart valves into a delivery device for implantation into a patient. More particularly, the present disclosure relates to devices and methods for loading a self-expanding collapsible heart valve into a delivery device for surgery.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like.

Collapsible prosthetic heart valves typically take the form of a valve structure mounted on a stent. The valve structure may include inner and outer cuffs near the annulus section of the stent. To place such valves into a delivery device and ultimately into a patient, the valve is generally first collapsed to reduce its circumferential size.

Present devices and methods for collapsing a stented valve having an outer cuff have been unsatisfactory as the forces required to load the collapsed valve into the delivery device have been undesirably high due to the larger collapsed size of the valve due to the additional bulk of the outer cuff. Additionally, the outer cuff of the valve may have a tendency to catch on an edge of the delivery device. These issues make it difficult to successfully load the valve in the delivery device without damage to the heart valve or delivery device, and in a manner that will allow for an easy and accurate deployment of the heart valve upon delivery.

Further, as the heart valve is collapsed, the struts of the stent may become entangled with one another, specifically in the aortic section of the valve, making it more difficult and time-consuming to load the valve in the delivery device due to the struts needing to be detangled before loading. It would therefore be beneficial to provide devices and methods for collapsing a stented heart valve using apparatus and techniques that overcome these deficiencies. Such devices and methods would allow for a successful and efficient loading of the heart valve in the delivery device.

BRIEF SUMMARY OF THE INVENTION

One aspect of the present disclosure provides devices for collapsing a prosthetic heart valve. According to one embodiment, the device includes a compression member including a support having a central axis and a plurality of arms connected to the support, each of the arms having an inner surface facing the central axis, a pair of side edges, and a free end, the arms being pivotable between a first orientation in which the side edges of adjacent arms are spaced apart from one another and a second orientation in which the side edges of the adjacent arms contact one another; and a translating member assembled to the compression member and movable along the arms from an initial position in which the arms are in the first orientation to a final position in which the arms are in the second orientation, movement of the translating member from the initial position to the final position pivoting the arms from the first orientation to the second orientation.

Another aspect of the present disclosure provides methods for collapsing a prosthetic heart valve. According to one embodiment, the method includes inserting the prosthetic heart valve in an expanded condition into an opening of a compression member, the compression member including a support having a central axis and a plurality of arms pivotably connected to the support, each arm having a free end and a pair of side edges, the plurality of arms being in a first orientation with the side edges of adjacent arms spaced apart from one another; and pivoting the plurality of arms from the first orientation to a second orientation in which the side edges of the adjacent arms contact one another, the pivoting step compressing the prosthetic heart valve from the expanded condition to a collapsed condition.

According to another embodiment in which the prosthetic heart valve includes a stent having struts, the method includes inserting a separation tool into an opening of a loading base, the separation tool including a shaft having a plurality of ribs extending along a length of the shaft and projecting radially outward from the shaft, adjacent ribs defining channels sized to receive selected ones of the struts; inserting the prosthetic heart valve into the opening; and collapsing the prosthetic heart valve so that the selected ones of the struts are received within respective ones of the channels of the separation tool and separated from one another by the ribs.

BRIEF DESCRIPTION OF THE DRAWINGS

Various embodiments of the presently disclosed prosthetic heart valve may be more fully understood with reference to the following detailed description when read with the accompanying drawings, in which.

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise or axial direction refers to a direction parallel to a longitudinal axis passing through the center of the stent or heart valve from the inflow end to the outflow end. When used herein in the context of a prosthetic heart valve, or a component thereof, the circumferential direction refers to a direction extending along the circumference of the prosthetic heart valve.

Figure 1:
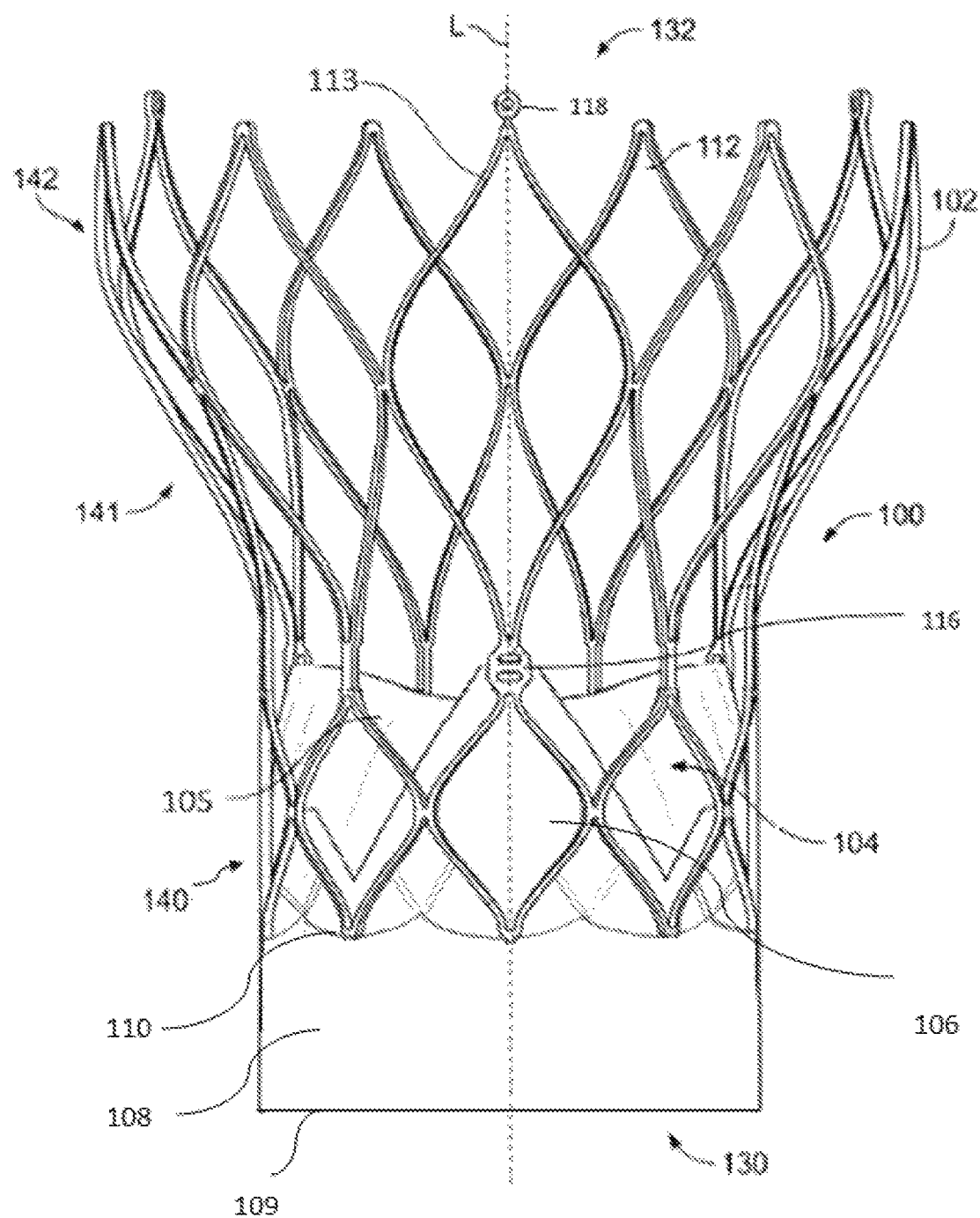
FIG. 1 is a front view of a collapsible prosthetic heart valve according to the prior art.

FIG. 1 shows a collapsible stent-supported prosthetic heart valve 100 in an expanded condition. The prosthetic heart valve 100 includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded configuration in comparison to the transverse cross-section of aortic section 142 in the expanded configuration. A transition section 141 may taper outwardly from annulus section 140 to aortic section 142. Each of the sections of stent 102 includes a plurality of struts 113 forming cells 112 connected to one another in one or more annular or ring-shaped rows around the stent. For example, as shown in FIG. 1, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells 112 in aortic section 142 may be larger than the cells in annulus section 140 so as to better enable prosthetic heart valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to a collapsed condition, and shortens in the direction of longitudinal axis L as the cells expand when the stent transitions from the collapsed condition to the expanded condition. Although not shown in FIG. 1, struts 113 near the distal or outflow end 132 of stent 102 may curve slightly inwardly.

Stent 102 may include one or more retaining elements 118 at outflow end 132, the retaining elements being sized and shaped to cooperate with retaining structures provided on a delivery device (not shown). The engagement of retaining elements 118 with the retaining structures on the delivery device may help maintain prosthetic heart valve 100 in assembled relationship with the delivery device, minimize longitudinal movement of the prosthetic heart valve relative to the delivery device during unsheathing or resheathing procedures, and help prevent rotation of the prosthetic heart valve relative to the delivery device as the delivery device is advanced to the target location and during deployment. One such delivery device is described in U.S. Patent Publication No. 2012/0078352, filed Aug. 18, 2010, the entire disclosure of which is hereby incorporated by reference herein.

Stent 102 may also include a plurality of commissure attachment features 116 for mounting the commissures of the valve assembly to the stent. As can be seen in FIG. 1, each commissure attachment feature may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures that facilitate the suturing of the leaflet commissures to stent 102.

Stent 102 may be formed as a unitary structure, for example, by laser cutting or etching a tube of a superelastic and/or shape-memory metal alloy, such as a nickel-titanium alloy of the type sold under the designation nitinol. Such a unitary structure may be referred to as a "non-woven" structure in that it is not formed by weaving or winding one or more filaments.

Prosthetic heart valve 100 includes a valve assembly 104 positioned in the annulus section 140 of stent 102. Valve assembly 104 includes a plurality of leaflets 105 that collectively function as a one way valve by coapting with one another. An inner cuff 106 may be positioned on the luminal surface of stent 102 surrounding leaflets 105. Although cuff 106 is shown in FIG. 1 as being disposed on the luminal or inner surface of annulus section 140, the cuff may be disposed on the abluminal or outer surface of the annulus section, or may cover all or part of either or both of the luminal and abluminal surfaces of the annulus section. Cuff 106 may have a zig-zag structure at its outflow end, following certain stent struts 113 up to commissure attachment features 116 and other stent struts closer to the inflow end of the stent at circumferential positions between the commissure attachment features.

Prosthetic heart valve 100 may also include an outer cuff 108 disposed radially outward of inner cuff 106 on the abluminal or outer surface of annulus section 140. Inner cuff 106 and outer cuff 108 may be formed separately from one another. Outer cuff 108 may be a single piece of material having a substantially rectangular shape with a proximal edge 109 and a distal edge 110, and may be wrapped around the circumference of stent 102 at the inflow end of the stent so as to overlap in the longitudinal direction of the stent with inner cuff 106. The proximal edge 109 of outer cuff 108 may be coupled to stent 102 and/or to cuff 106 at or near the inflow end of the stent, for example by a continuous line of sutures (not shown), so that retrograde blood flow entering the space between the outer cuff and the inner cuff cannot pass in the retrograde direction beyond these combined structures. In order to allow retrograde blood flow to enter the space between outer cuff 108 and inner cuff 106, the distal edge 110 of the outer cuff may be attached, for example with sutures, to stent 102 and/or to inner cuff 106 at locations that are spaced apart in the circumferential direction of the stent. Although the foregoing description uses the term "inner" in connection with cuff 106, that is merely intended to indicate that cuff 106 is positioned radially inward of outer cuff 108. Inner cuff 106 may be located either on the luminal or abluminal side of stent 102, or on both sides.

Although inner cuff 106 and outer cuff 108 are described above as separate pieces of material joined to stent 102 and to each other, they may be formed integrally with one another from a single piece of material that is wrapped around the inflow end of stent 102, with the distal edge 110 of the outer cuff joined to the stent and/or to the inner cuff at attachment points. With this configuration, the proximal edge 109 of outer cuff 108 does not need to be sutured to stent 102, although it still may be preferable to provide such attachment. Outer cuff 108 may have an axial height measured from its proximal edge 109 to its distal edge 110 that is approximately half the axial height of a cell 112 in the proximal-most row of cells in stent 102, the axial height being measured along the major axis of the cell between two of its apices when the cell is in an expanded condition. However, outer cuff 108 may have other suitable heights, such as the full axial height of a cell 112 in the proximal-most row of cells, or more or less than the full axial height of a cell in the proximal-most row of cells.

Figure 2A:
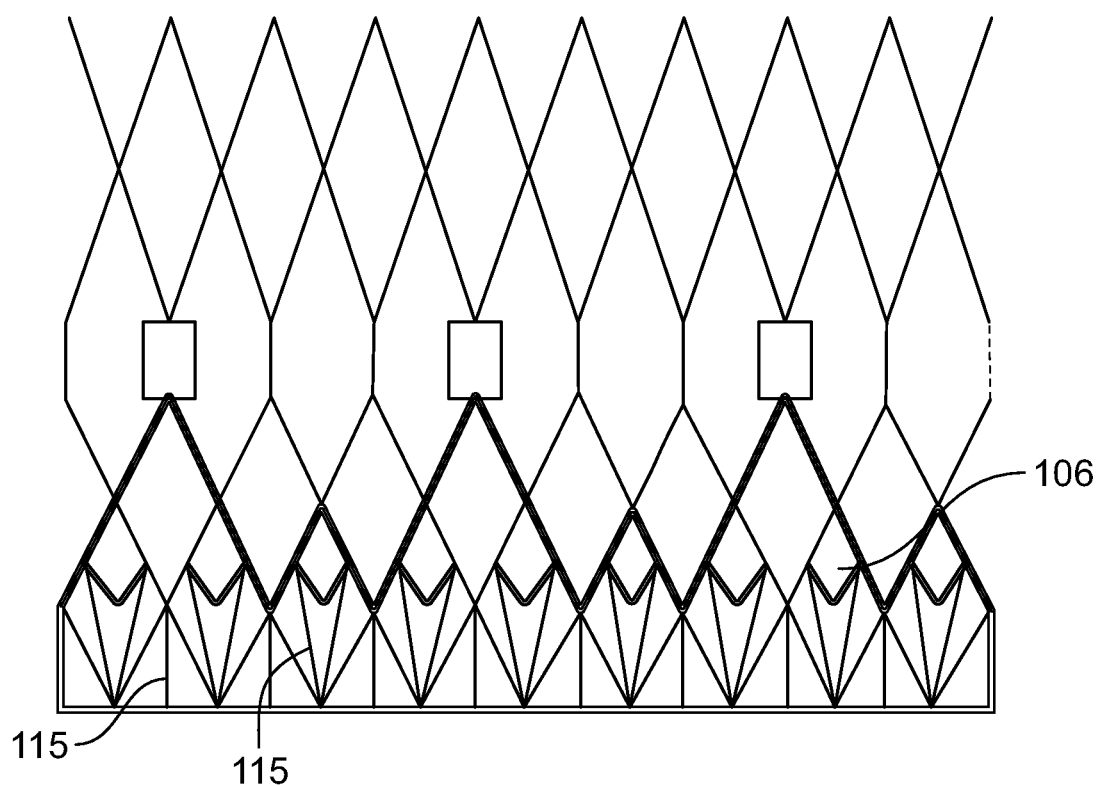
FIGS. 2A-B are schematic views of the stent and cuff of a prosthetic heart valve according to an embodiment of the disclosure in a flattened condition.
Figure 2B:
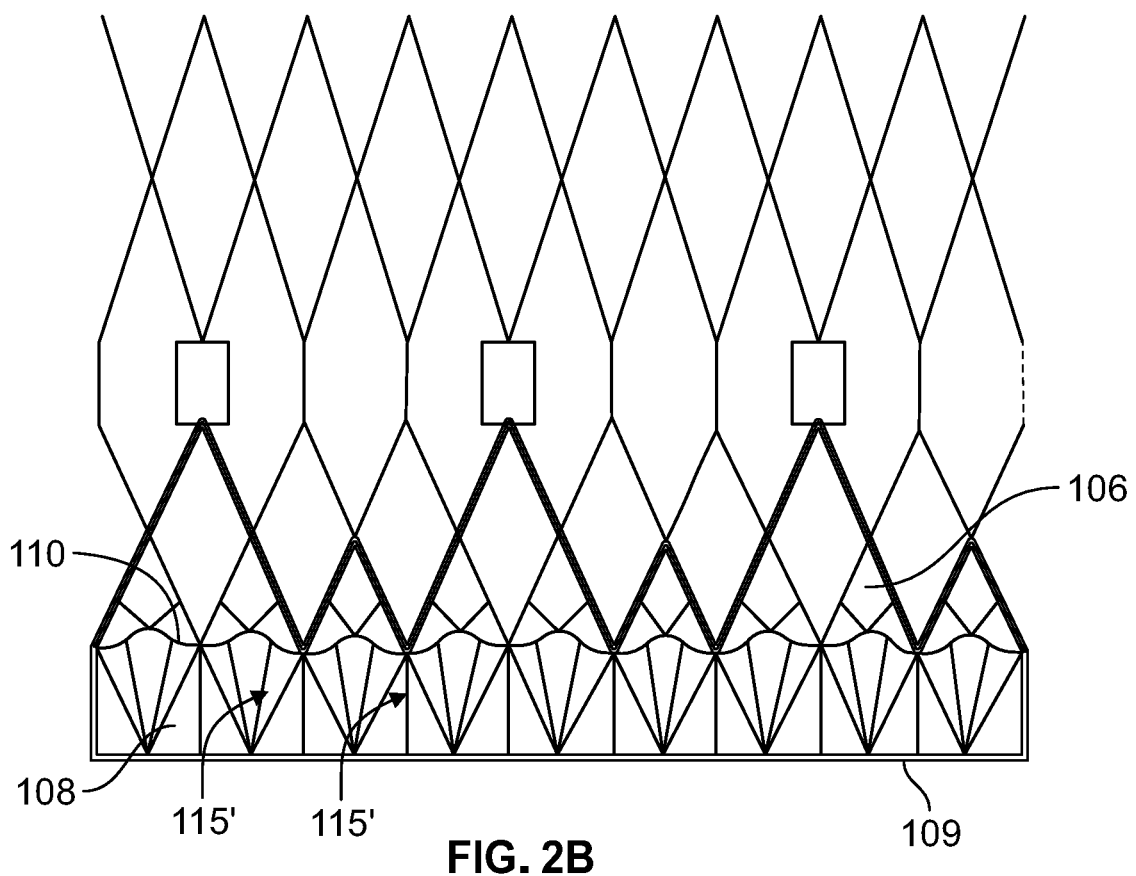

FIGS. 2A and 2B depict prosthetic heart valve 100 having fold lines for inner cuff 106 and outer cuff 108 according to embodiments of the disclosure. FIG. 2A depicts fold lines 115 for inner cuff 106, while FIG. 2B depicts fold lines 115' for outer cuff 108. Fold lines 115, 115' facilitate the folding of inner cuff 106 and outer cuff 108 as prosthetic heart valve 100 collapses during the loading of the valve into the delivery device.

Inner cuff 106 and outer cuff 108 may be formed of the same or different materials, including any suitable biological material or polymer such as, for example, polytetrafluroethylene (PTFE), ultra-high molecular weight polyethylene (UHMWPE), polyurethane, polyvinyl alcohol, silicone, or combinations thereof.

Prosthetic heart valve 100 may be loaded in any suitable delivery device for delivery to a desired target site in a patient. Methods of loading a prosthetic heart valve in a delivery device are disclosed in U.S. Pat. No. 8,973,234, issued on Mar. 10, 2015, and titled "Assembly and Method for Loading a Self-Expanding Collapsible Heart Valve," the disclosure of which is hereby incorporated by reference herein in its entirety. During delivery, prosthetic heart valve 100 is disposed inside the delivery device in the collapsed condition. Once the delivery device has reached the target site, the user may deploy prosthetic heart valve 100. Upon deployment, prosthetic heart valve 100 expands into secure engagement within the native annulus.

Figure 3:
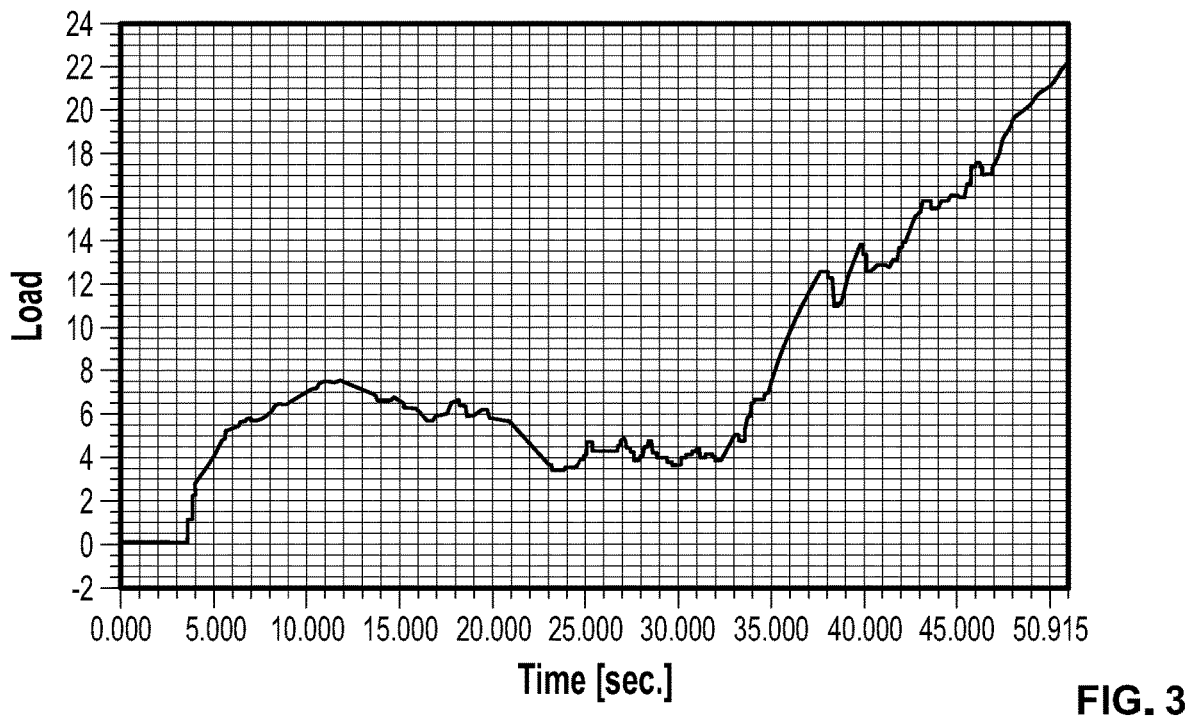
FIG. 3 is a graph showing loading forces encountered during loading of a collapsible prosthetic heart valve having an outer cuff into a delivery device.
Figure 4:
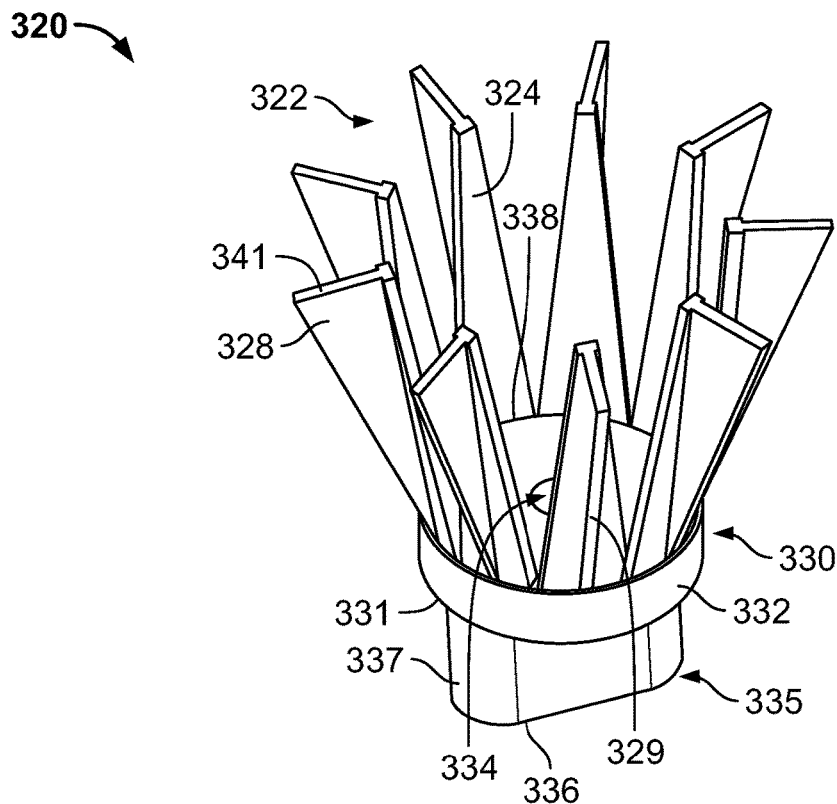
FIG. 4 is a schematic perspective view of a compression member of a loading assembly according to an embodiment of the present disclosure, the compression member being in an expanded condition.
Figure 5:
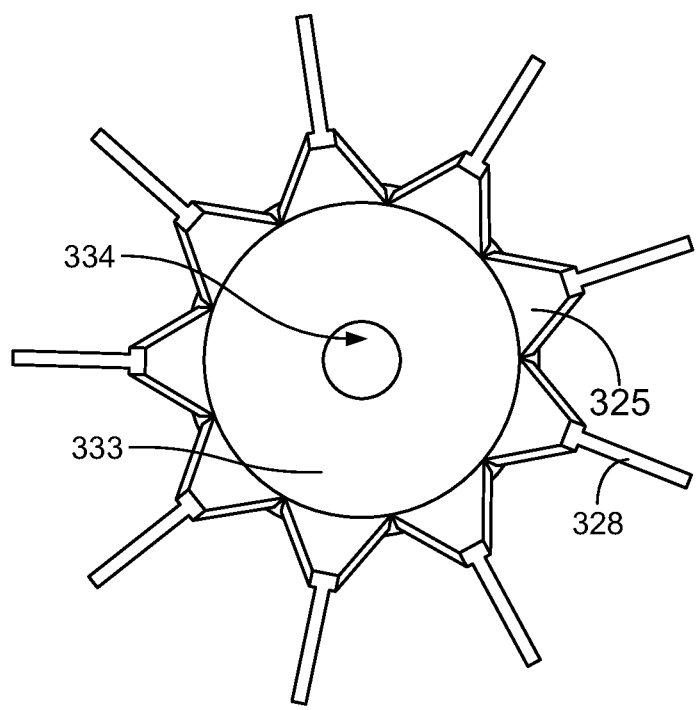
FIG. 5 is a top view of the compression member of FIG. 4.
Figure 6:
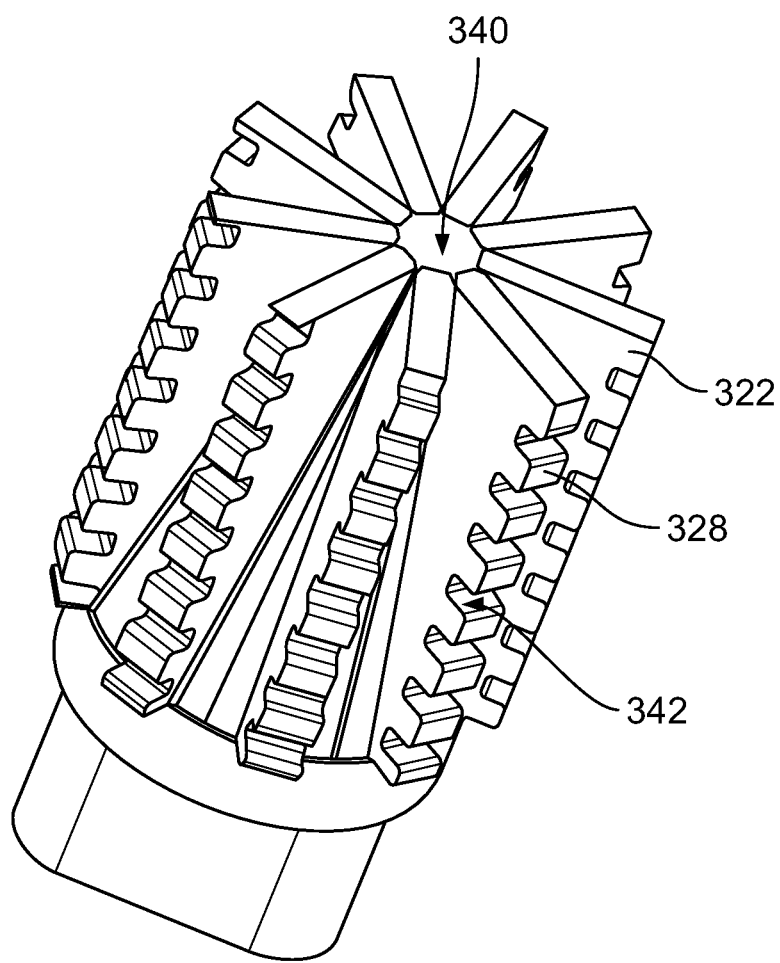
FIG. 6 is a perspective view of the compression member of FIG. 4 in a collapsed condition.

Additionally, it is preferable to collapse the prosthetic heart valve 100 at the latest possible time before surgical implantation. In order to effectively limit the time period prosthetic heart valve 100 is collapsed, the collapsing process is preferably conducted in the operating arena by the surgeon, interventional cardiologist, or surgical assistant using a loading assembly 300, described below. While loading prosthetic heart valve 100 into the delivery device, outer cuff 108 may catch on an edge or lip of the delivery device because the outer cuff extends outwardly from stent 102. When outer cuff 108 catches on an edge of the delivery device, the loading forces increase as shown in FIG. 3. The peak force corresponds to the catching of at least a portion of outer cuff 108 on the delivery device. Thus, the loading forces may be undesirably high, making it difficult to successfully load prosthetic heart valve 100 in the delivery device without damage to the heart valve or delivery device, and in a manner that will allow for an easy and accurate deployment of the heart valve upon delivery.

With reference to FIGS. 4-9, loading assembly 300, according to an embodiment of the present disclosure, includes a funnel or compression member 320 and a screw nut or translating member 350 that cooperate to uniformly compress the outer diameter of stent 102 and push outer cuff 108 through the struts 113 of cells 112 to the inner diameter of stent 102. This results in stent 102 having a smaller outer diameter than the inner diameter of the distal sheath of the delivery device and prevents outer cuff 108 from catching on an edge of the delivery device.

Compression member 320 includes a generally oblong base 335 having a lower surface 336 and a side surface 337. Base 335 provides stability to compression member 320 when it is placed on a flat surface. A support 330 coupled to the top of base 335 has a substantially round profile with a lower surface 331, an upper surface 333, and an annular wall 332. The top edge of wall 332 extends above upper surface 333, providing a recess in the top of support 330. An aperture 334 extends through base 335 and support 330 along a longitudinal axis of compression member 320, and is sized for receiving the distal end of the delivery device therethrough.

Compression member 320 further includes a plurality of arms 322 pivotally coupled around the circumference of the upper surface 333 of support 330 adjacent annular wall 332. Each of arms 322 includes an elongated, generally triangular wall segment 324 extending from a wide base at its connection to the upper surface 333 of support 330 to a narrowed tip adjacent its free end 341. A surface 325 of wall segment 324 faces radially inward toward the longitudinal axis of compression member 320, and a camming rib 328 projects radially outward from a surface of wall segment 324 opposite surface 325. Each of ribs 328 has a tapered outer edge 329 which provides the rib with a generally triangular shape extending from a narrow end adjacent the upper edge of annular wall 332 to a wide end adjacent the free end 341 of arm 322. The outer edges 329 of ribs 328 include a plurality of grooves 342 extending transverse to the elongation direction of the rib, the purpose of which will be described below. Arms 322 may be connected to the upper surface 333 of support 330 by a living hinge 338 enabling the arms to pivot from an expanded condition, shown in FIGS. 4 and 5, to a collapsed condition, shown in FIG. 6. In the collapsed condition, wall segments 324 mate with one another in edge-to-edge fashion so that surfaces 325 collectively form a substantially conical surface above the upper surface 333 of support 330. Surface 325 of wall segment 324 may be slightly concave, or in other examples, may be flat.

In the illustrated embodiment, compression member 320 has nine arms 322; however in other examples, the compression member may have more or fewer arms. The size of arms 322 and the space between them in the expanded condition of compression member 320 may be greater or smaller than shown depending on the number of arms on the compression member. Compression member 320 may be formed of a flexible polymer such as, for example, polycarbonate.

Figure 7:
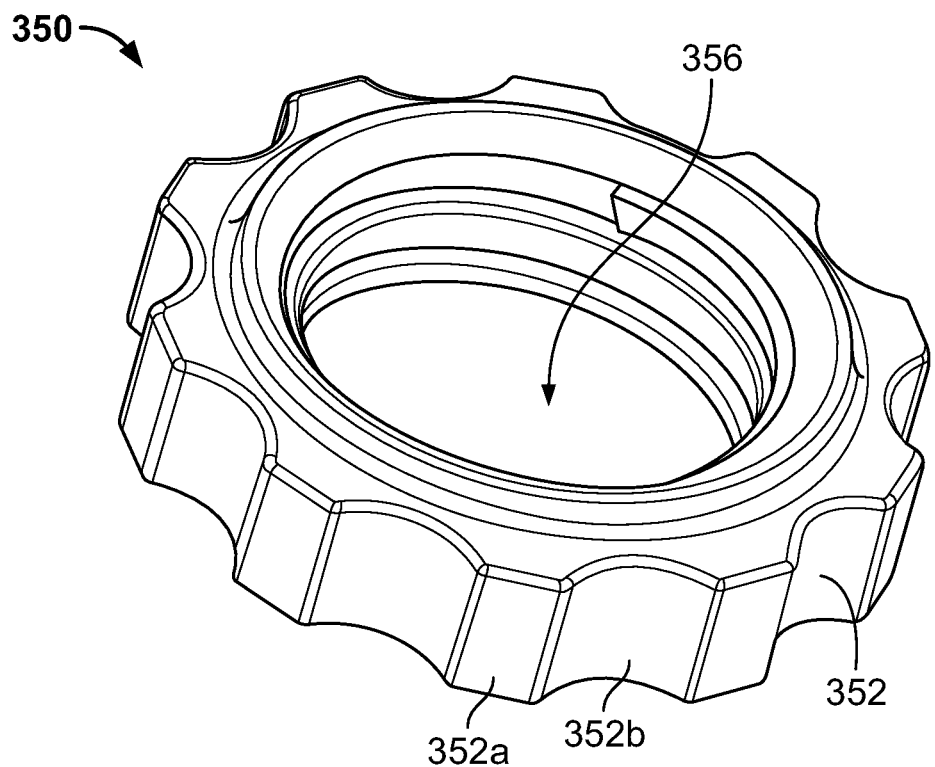
FIG. 7 is a perspective view of a translating member of the loading assembly according to an embodiment of the present disclosure.

FIG. 7 is a perspective view of translating member 350. Translating member 350 is generally in the form of a nut, and has a large threaded aperture 356 and an outer circumference 352 with a plurality of projections 352a separated by curved recesses 352b. The threads in aperture 356 are sized to threadingly engage the grooves 342 on the outer edges 329 of ribs 328 during the operation of loading assembly 300. Although the outer circumference of translating member 350 is shown with alternating projections 352a and curved recesses 352b, the outer circumference may include alternate features, such as knurling, that assist the user in gripping and rotating the translating member relative to compression member 320. Translating member 350 is adapted to slide onto compression member 320 from base 335 and move in a distal direction toward the free ends 341 of the arms 322 of the compression member as it is rotated relative to same. The grooves 342 on translating member 350 may not be provided along the entire length of outer edges 329 up to the free ends 341 of arms 322 so that translating member 350 cannot translate off compression member 320. Translating member 350 may be formed of a polymer, specifically a self-lubricating polymer such as, for example, polyoxymethylene, so that the translating member easily advances along the arms 322 of compression member 320 as it is rotated.

Figure 8A:
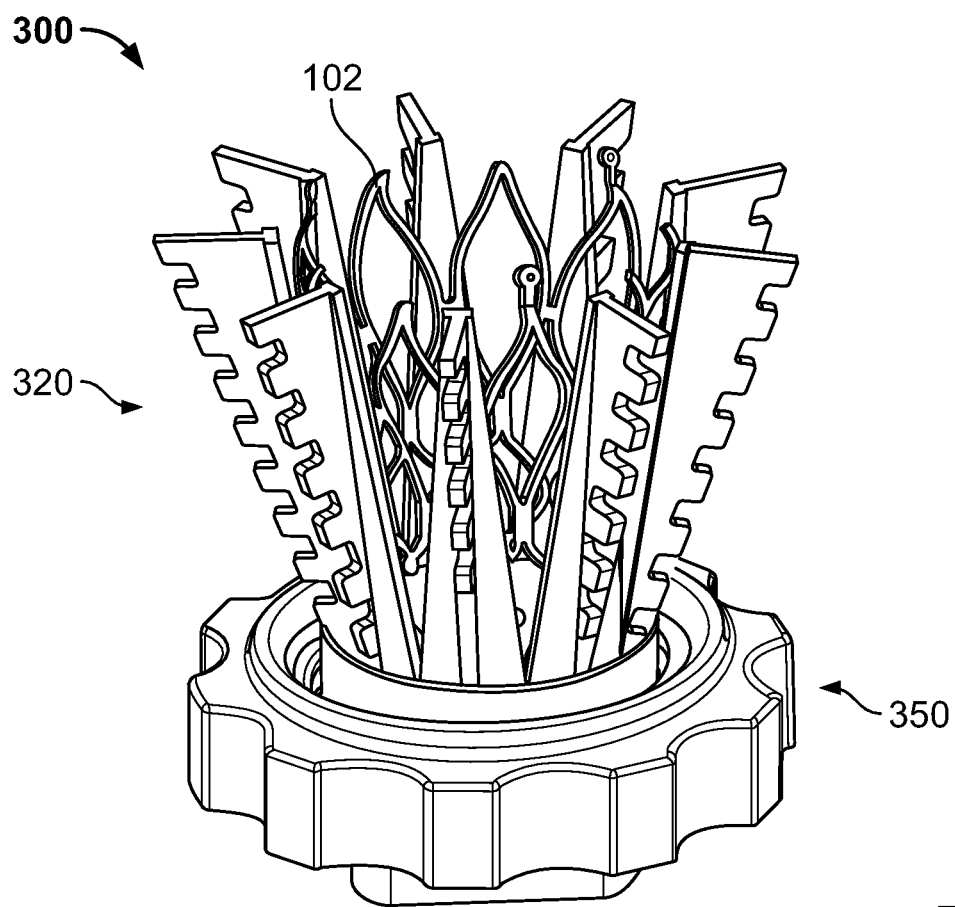
FIGS. 8A-B are schematic perspective and top views, respectively, of the loading assembly according to an embodiment of the present disclosure with a valve stent positioned thereon, the loading assembly being in an expanded condition.
Figure 8B:
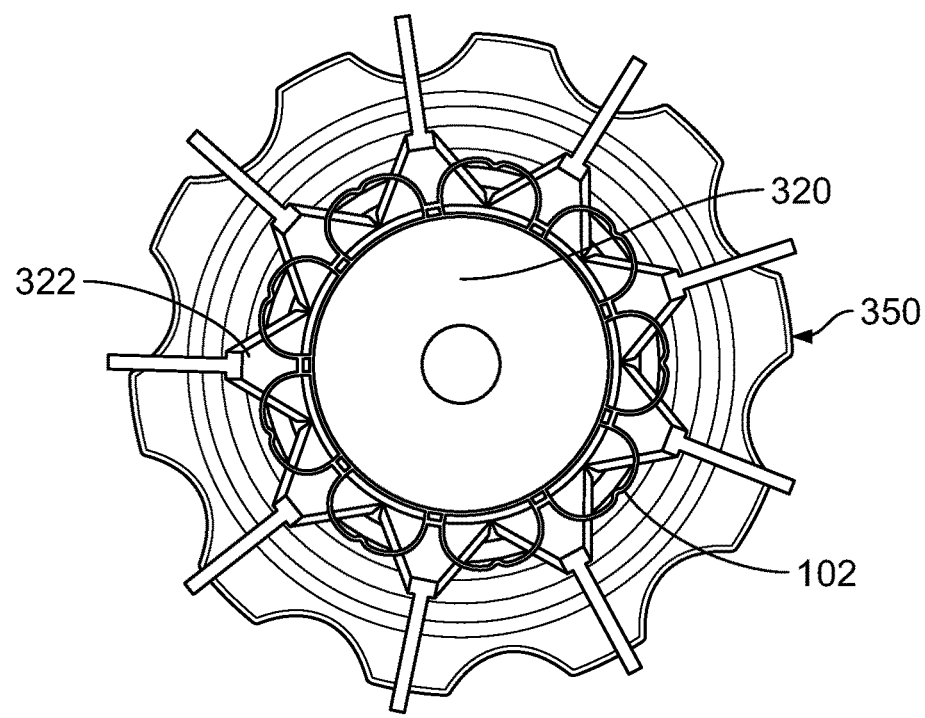
Figure 9A:
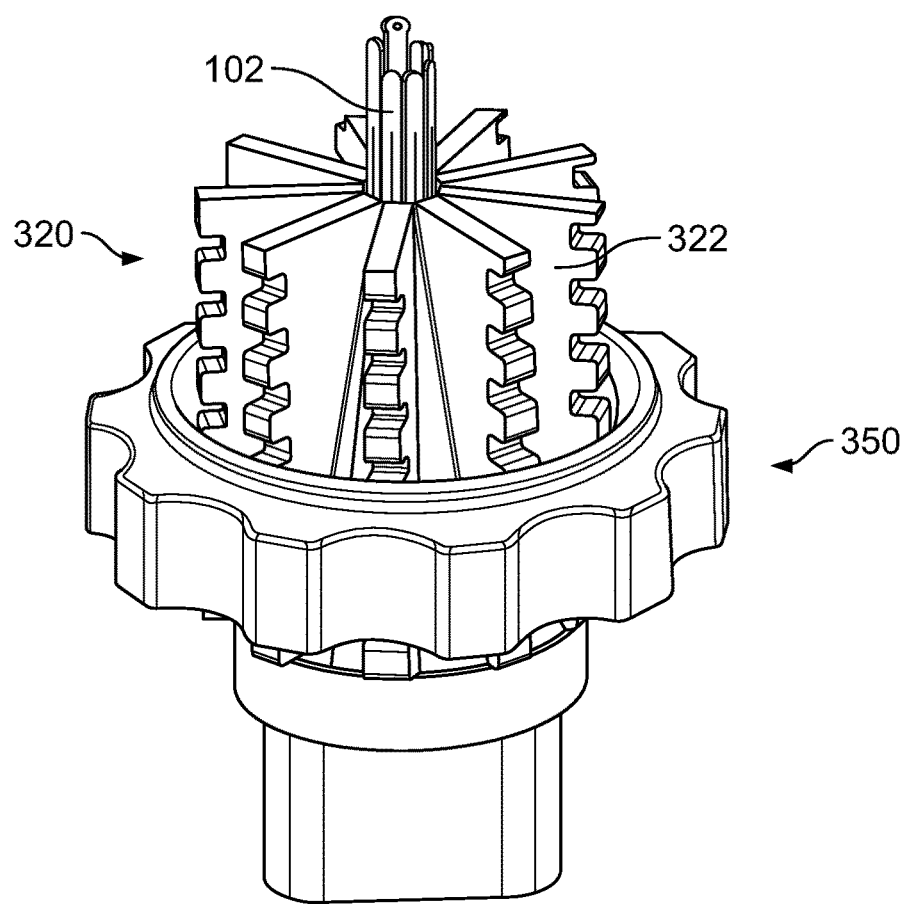
FIGS. 9A-B are schematic perspective and top views, respectively, of the loading assembly of FIGS. 8A-B in a collapsed condition.
Figure 9B:
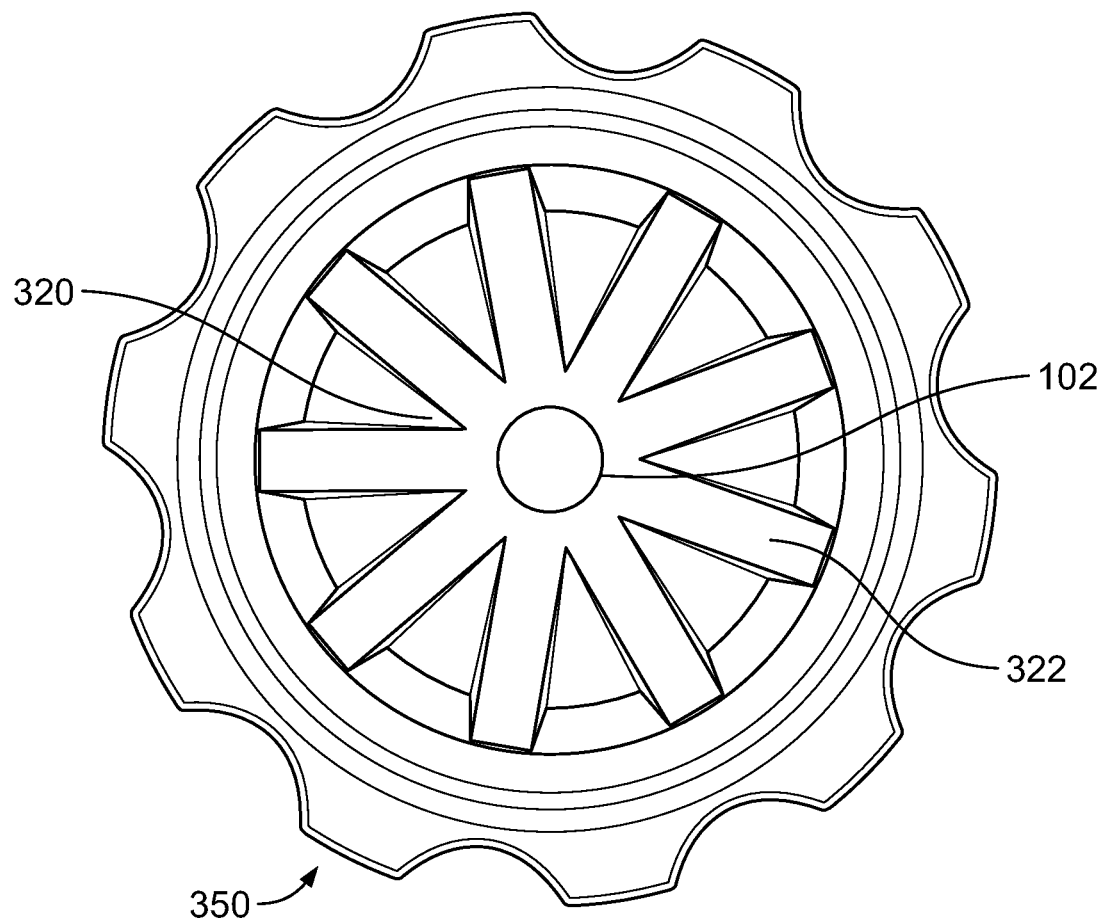

FIGS. 8A-B show loading assembly 300 in the expanded condition with the annulus end 130 of prosthetic heart valve 100 resting on the upper surface 333 of the support 330 of compression member 320 and translating member 350 in an initial position around the support. Prosthetic heart valve 100 is preferably positioned on support 330 so that the fold lines 115' of outer cuff 108 are radially aligned with the arms 322 of compression member 320. In this initial position, heart valve 100 extends from the upper surface 333 of support 330 to the free ends 341 of arms 322. In other examples, arms 322 may be longer than heart valve 100, however, it will be appreciated that the arms preferably are at least as long as the heart valve so that the entire heart valve is collapsed as loading assembly 300 is moved from the expanded condition to the collapsed condition. From this initial position, translating member 350 may be rotated in a clockwise or counterclockwise direction (depending on the angle of the threads on the translating member) until the threads in aperture 356 engage the grooves 342 in the outer edges 329 of ribs 328. As the rotation of translating member 350 continues, the translating member will advance along arms 322, engaging ever wider sections of ribs 328 to urge the arms radially inward, progressively collapsing heart valve 100. The inward movement of arms 322 pushes on outer cuff 108 at the fold lines 115' thereof. As outer cuff 108 folds along fold lines 115', portions of the outer cuff will be pushed between the struts 113 forming cells 112 to the interior of stent 102. The continued rotation and advancement of translating member 350 causes arms 322 to continue to move inward until the lateral edges of the arms are fully engaged with one another and the free ends 341 of the arms form a continuous substantially circular aperture 340, as shown in FIGS. 9A-B. At this junction, further rotation and advancement of translating member 350 may be prevented by the lack of grooves 342 near the free ends 341 of arms 322. In this fully collapsed condition of compression member 320, heart valve 100 is collapsed to a diameter that is smaller than the inner diameter of the delivery device. As stent 102 elongates as it collapses, the aortic end 132 of the stent may protrude from aperture 340 in this fully collapsed condition. Stent 102 may then be attached to the delivery device in a known manner Because a large portion of outer cuff 108 is urged to the interior of stent 102, the outer cuff may not catch on an edge of the delivery device as it is loaded therein. As a result of this and of the controlled collapse of prosthetic heart valve 100 to a small profile through the use of compression member 320 and translating member 350, the forces required to load the collapsed heart valve into the delivery device may be lower.

Figure 10:
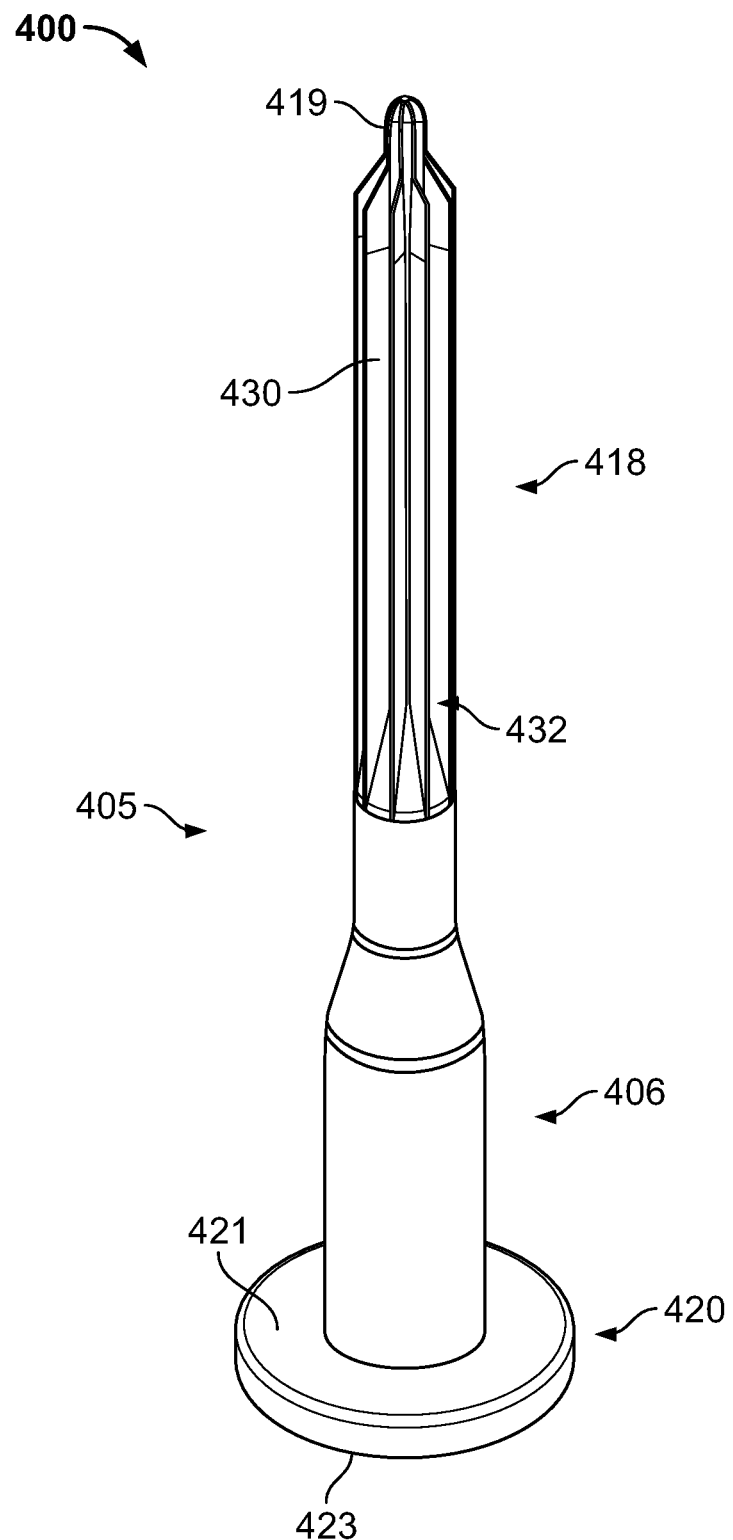
FIG. 10 is a perspective view of a separation tool, according to an embodiment of the present disclosure.

FIG. 10 depicts a separation tool 400 according to another aspect of the present disclosure. Separation tool 400 has a base 420 with a substantially planar lower surface 423 to enable the separation tool to stand upright on a flat surface. A shaft 405 projects from an upper surface 421 of base 420. Shaft 405 may have a longitudinal axis and a diameter that is less than the diameter of aperture 340 in the fully collapsed condition of compression member 320, such that the shaft can fit through the aperture when the compression member is in the fully collapsed condition. Shaft 405 has a proximal section 406 adjacent base 420 and a distal section 418 spaced from the base and terminating with a narrowed distal tip 419. In the illustrated embodiment, proximal section 406 may have a larger diameter than distal section 418, and shaft 405 may be tapered from the proximal section to the distal section. In other embodiments, however, there may be a more abrupt transition between the larger diameter of proximal section 406 and the smaller diameter of distal section 418. In still further embodiments, shaft 405 may have a substantially constant diameter along its length.

The distal section 418 of shaft 405 includes a plurality of ribs 430 extending along its length. Ribs 430 project radially outward so as to define elongated channels 432 between each pair of adjacent ribs. Channels 432 are sized to receive the struts 113 and the retaining elements 118 at the outflow end 132 of stent 102. In the illustrated embodiment, shaft 405 has nine ribs 430 defining nine channels 432 in which struts 113 may be positioned; however, in other examples, there may be more or fewer ribs and thus channels. By positioning the struts 113 and retaining elements 118 at the outflow end 132 of stent 102 in channels 432, ribs 430 keep the struts in proper alignment and prevent the struts and retaining elements from contacting and/or becoming entangled with one another.

Figure 11:
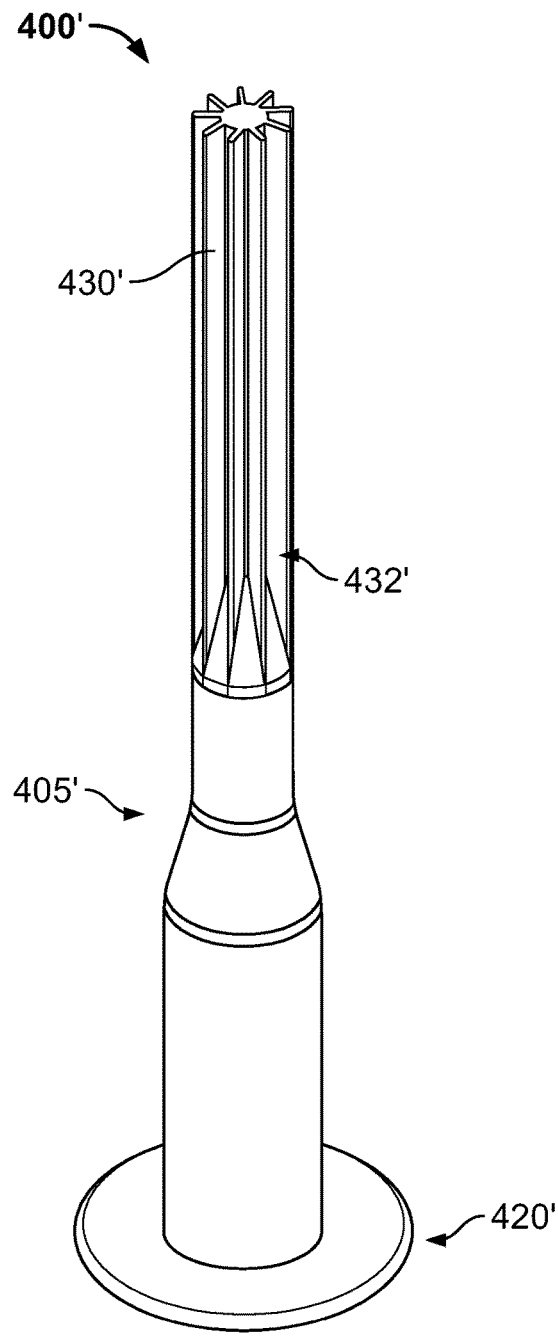
FIG. 11 is a perspective view of another separation tool, according to an embodiment of the present disclosure.
Figure 12:
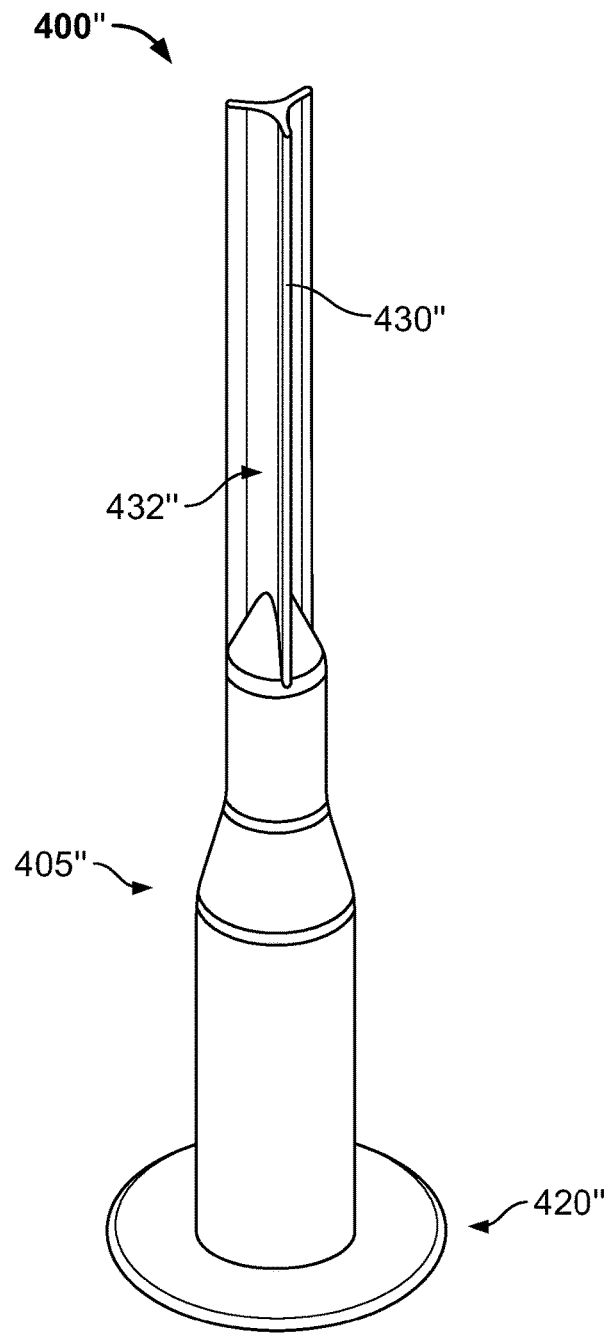
FIG. 12 is a perspective view of another separation tool, according to an embodiment of the present disclosure.
Figure 13:
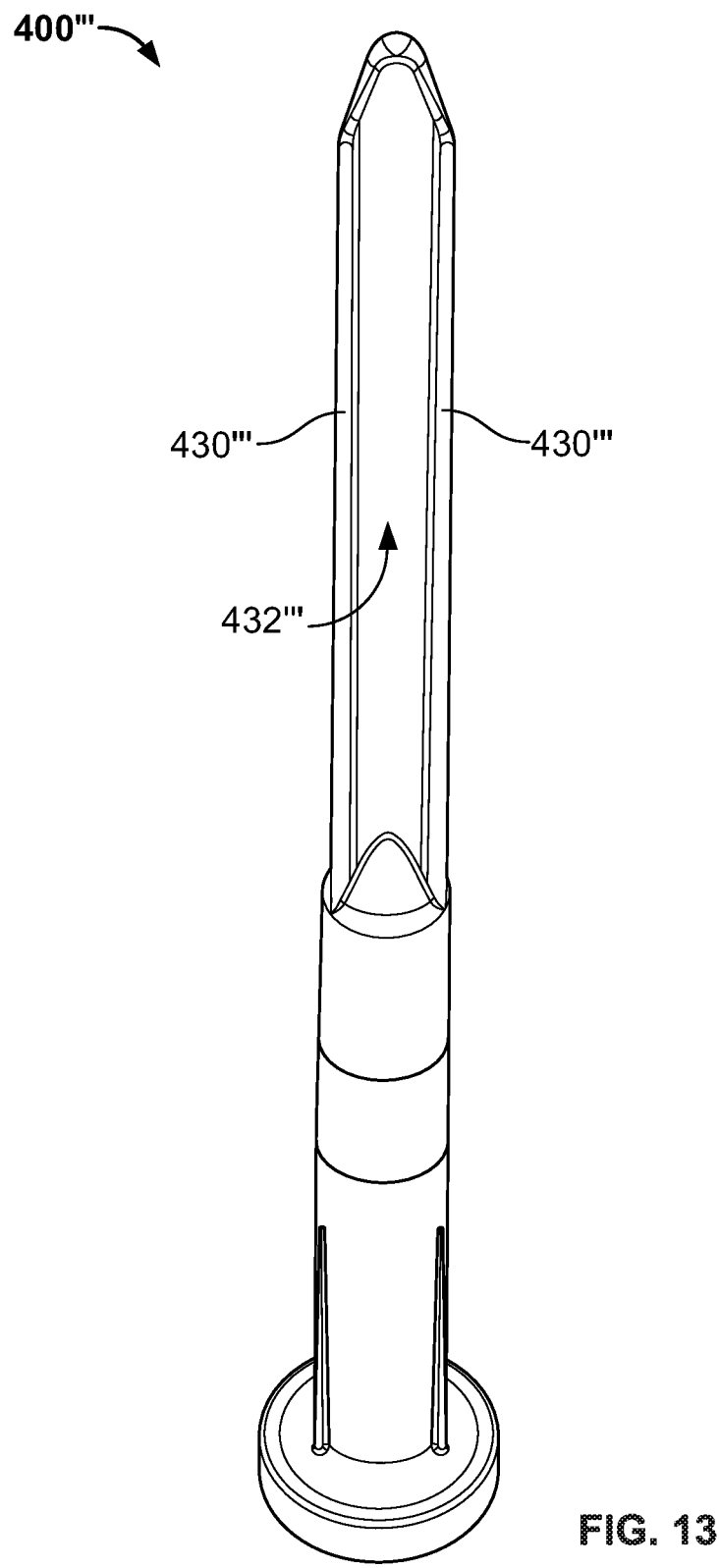
FIG. 13 is a perspective view of another separation tool, according to an embodiment of the present disclosure.

FIGS. 11-13 show separation tools 400', 400", and 400''', which share similar features and functions with separation tool 400 with certain exceptions, as will be described herein. For example, separation tools 400' and 400" do not include narrowed distal tips, such as the distal tip 419 of separation tool 400. Further, as shown in FIGS. 12 and 13, separation tools 400" and 400''' each have three ribs 430" defining three channels 432" and 432''' respectively. As a result, ribs 430" and 430''' may separate those struts having retaining elements 118 or may separate three distinct groups of struts from one another.

Although described with reference to a specific number of ribs 430, each separation tool 400, 400', 400", 400''' may have more ribs or fewer ribs than shown. Further, in other examples, ribs 430 may have different shapes, so long as they are capable of separating the struts 113 of stent 102. Separation tools 400, 400', 400", 400''' may be monolithic, or alternatively, they may be comprised of individual components assembled to one another. Furthermore, the separation tools may be made of any strong, rigid material and may include a smooth and/or slightly lubricous surface finish to allow the struts to slide smoothly along the tool without scraping material off.

Separation tools 400, 400', 400", and 400''' may be used with various configurations of loading assemblies, including loading assembly 300 described above. Although the method of use of separation tool 400 will be described below, such description is also meant to be illustrative of the use of separation tools 400', 400", 400''' as well as other variations of separation tools having different rib configurations.

To use separation tool 400 with loading assembly 300 to collapse prosthetic heart valve 100, separation tool 400 is inserted through aperture 334 in base 335. Prosthetic heart valve 100 is then placed on the upper surface 333 of support 330 so that the outflow end 132 of the valve is nearer to the free ends 341 of arms 322 and the inflow end 130 of the valve rests on the support. The separation tool extends through the interior of prosthetic heart valve 100 until the distal section 418 of the separation tool projects beyond the outflow end 132 of the valve. Of course, the prosthetic heart valve can be positioned within the loading base prior to the insertion of the separation tool. Translating member 350 is then positioned around base 335 and rotated relative to compression member 320 such that it translates distally along the arms 322 of the compression member. Arms 322 pivot inwardly, which collapses prosthetic heart valve 100 to a smaller diameter and pushes at least a portion of outer cuff 108 between the cells 112 of stent 102. As stent 102 collapses, the struts 113 and retaining elements 118 at the outflow end 132 of the stent are positioned in and guided by the channels 432 between the ribs 430 of separation tool 400, preventing the struts of the stent from becoming tangled. With prosthetic heart valve 100 fully collapsed, separation tool 400 may be removed and the heart valve may then be attached to the delivery device.

Figure 14:
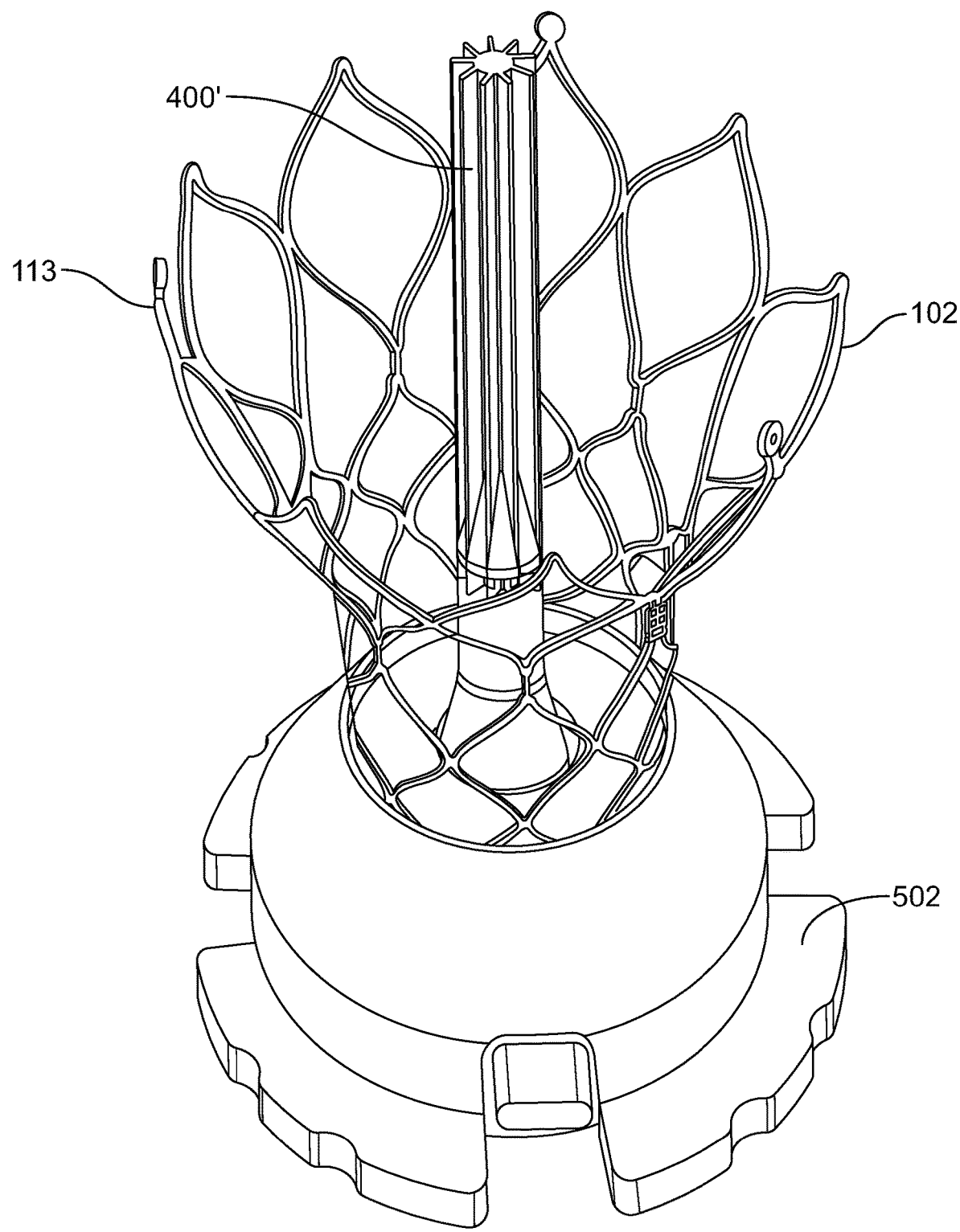
FIGS. 14-16 are perspective views showing the use of the separation tool of FIG. 11 in conjunction with a loading assembly.
Figure 15:
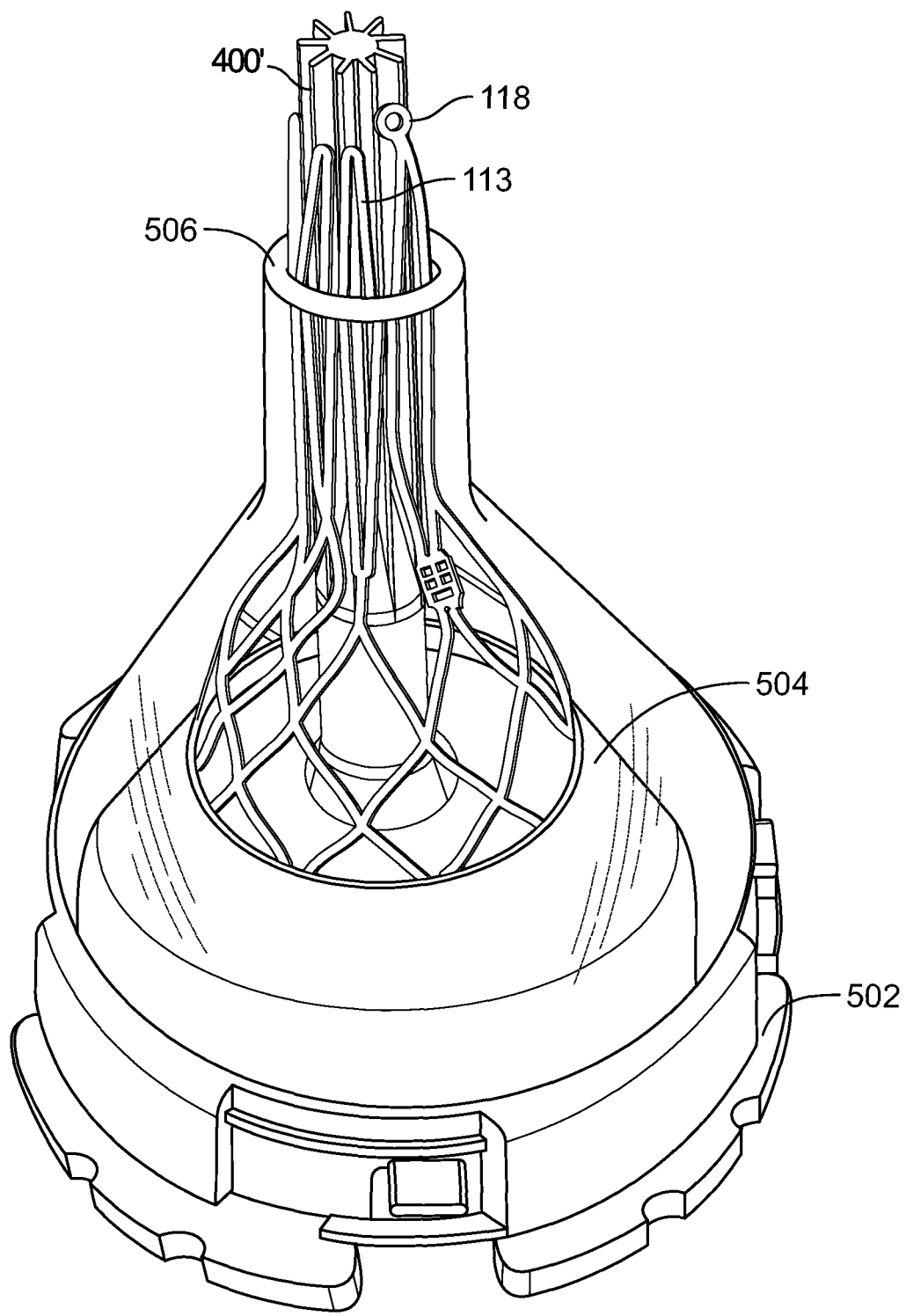
Figure 16:
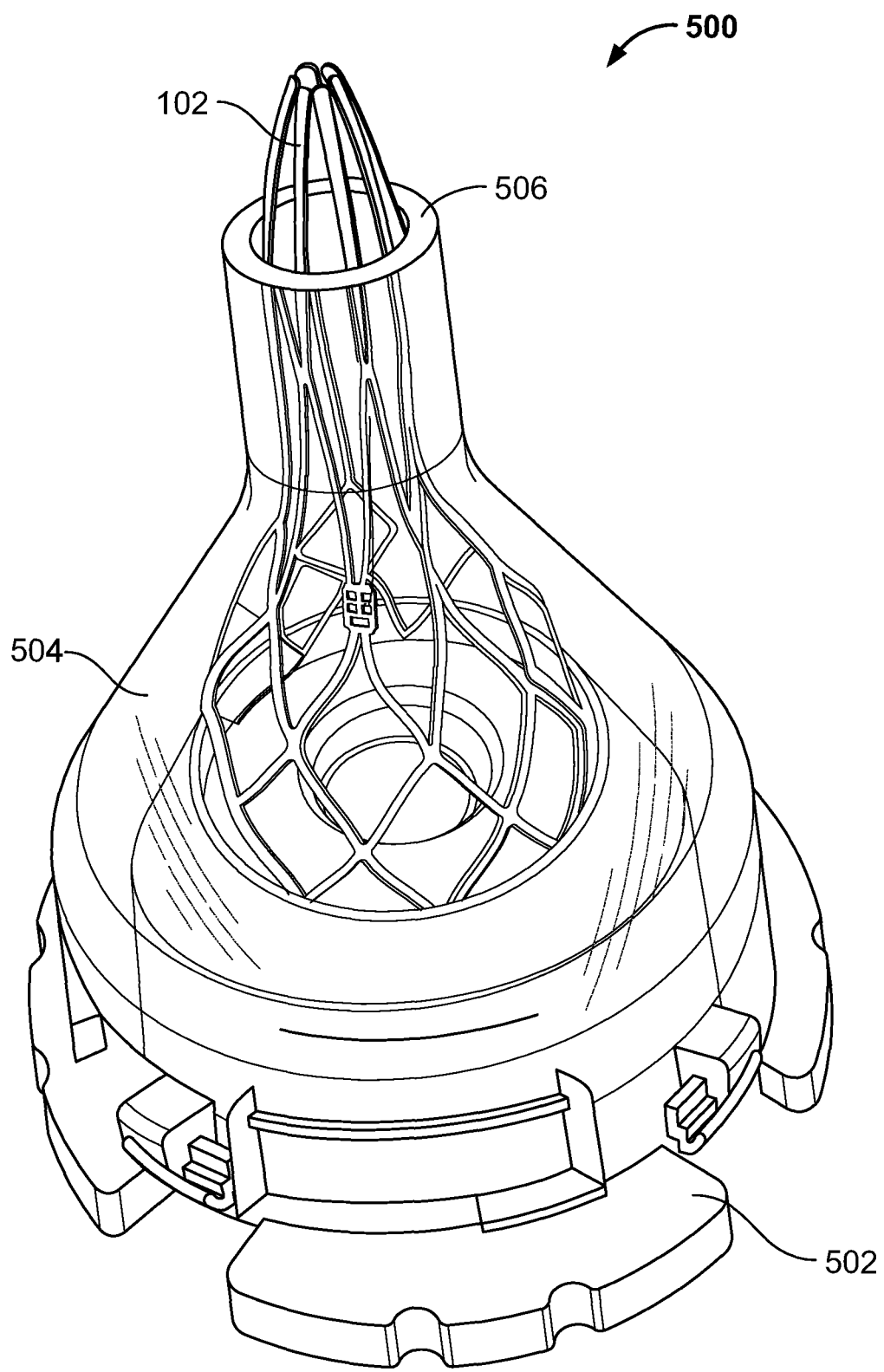

Any of separation tools 400, 400', 400", and 400''' may be used in conjunction with loading assemblies other than loading assembly 300, including loading assembly 500 shown in FIGS. 14-16. Loading assembly 500 and its use to collapse a prosthetic heart valve 100 are described in U.S. Pat. No. 8,973,234, mentioned above. Briefly, loading assembly 500 has a base 502 and a compression member 504. Separation tool 400' is inserted through an aperture (not shown) in the base. Prosthetic heart valve 100 (for simplicity, only the stent 102 of the prosthetic heart valve is shown in FIGS. 14-16) is then positioned on base 502 such that separation tool 400' extends through the interior of the prosthetic heart valve until the distal tip 419' of the separation tool is positioned beyond the outflow end 132 of the stent, as shown in FIG. 14. Compression member 504 may then be guided over prosthetic heart valve 100 and toward base 502. As base 502 and compression member 504 are moved toward one another, the funnel shape of the compression member gradually collapses prosthetic heart valve 100 until the outflow end 132 of stent 102 protrudes from the narrowed outlet 506 of the compression member, as shown in FIG. 15. As stent 102 collapses, the struts 113 and retaining elements 118 at the outflow end 132 of the stent are positioned in and guided by the channels 432' between the ribs 430' of separation tool 400'. Once prosthetic heart valve 100 has been fully collapsed, separation tool 400' may be removed and the heart valve may then be attached to the delivery device.

Figure 17:
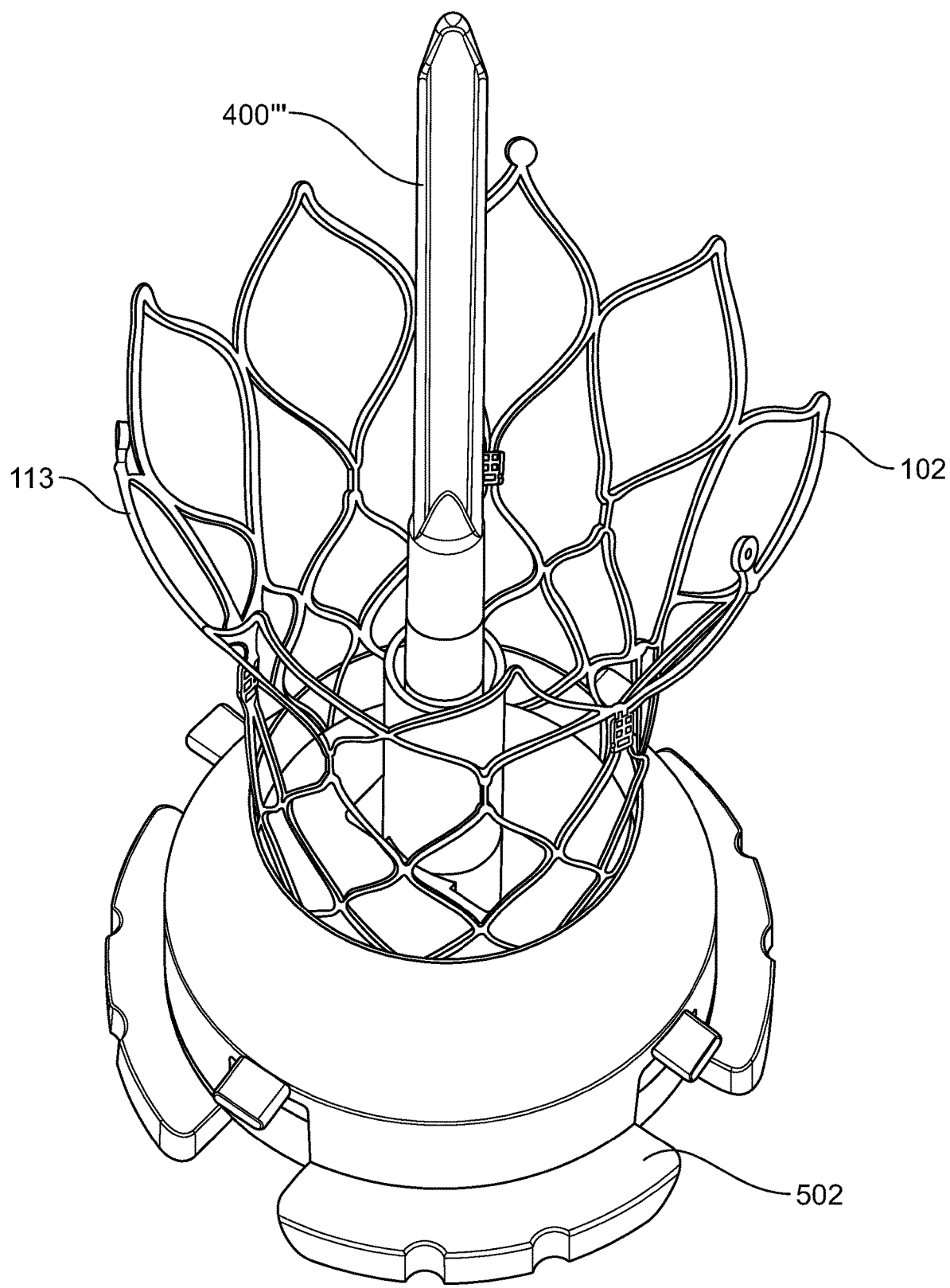
FIGS. 17-18 are perspective views showing the use of the separation tool of FIG. 13.
Figure 18:
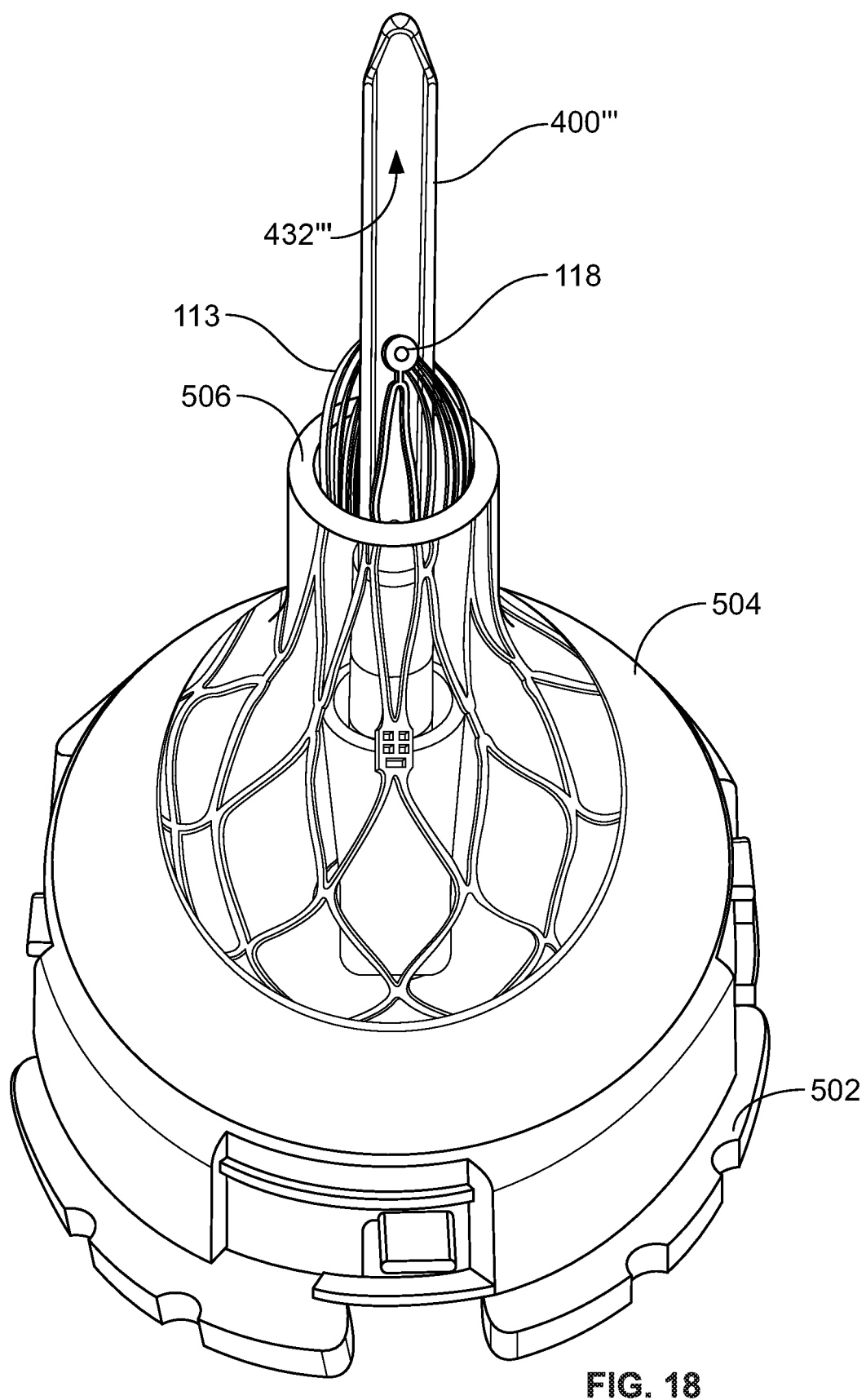

FIGS. 17-18 show loading assembly 500 in conjunction with separation tool 400''', which is used in substantially the same manner as described above with reference to separation tool 400'. As shown in FIG. 18, channels 432''' maintain separation of the retaining elements 118 of the stent from one another.

To summarize the foregoing, a first aspect of the disclosure describes a device for collapsing a prosthetic heart valve. The device includes a compression member including a support having a central axis and a plurality of arms connected to the support, each of the arms having an inner surface facing the central axis, a pair of side edges, and a free end, the arms being pivotable between a first orientation in which the side edges of adjacent arms are spaced apart from one another and a second orientation in which the side edges of the adjacent arms contact one another; and a translating member assembled to the compression member and movable along the arms from an initial position in which the arms are in the first orientation to a final position in which the arms are in the second orientation, movement of the translating member from the initial position to the final position pivoting the arms from the first orientation to the second orientation; and/or the free ends of the arms in the second orientation may define an aperture; and/or the inner surfaces of the arms may collectively define a compression surface in the second orientation of the arms, the compression surface decreasing uniformly in diameter from a first end adjacent the support to a second end adjacent the free ends of the arms; and/or each of the arms may extend in a length direction between the support and the free end of the arm and may include an outer side facing away from the central axis, the outer side including a plurality of grooves oriented transverse to the length direction and spaced apart from one another along a length of the arm; and/or the plurality of grooves on the arms may collectively define a threaded portion and the translating member may include threads engageable with the threaded portion so that rotation of the translating member relative to the compression member moves the translating member from the initial position toward the final position; and/or the threaded portion may extend from the support to a location spaced from the free ends of the arms; and/or the outer side of each of the arms may include a rib that tapers in thickness from a small thickness relatively close to the support to a large thickness relatively close to the free end of the arm; and/or each arm may be connected to the support by a living hinge.

Another aspect of the disclosure describes a method for collapsing a prosthetic heart valve, the method including inserting the prosthetic heart valve in an expanded condition into an opening of a compression member, the compression member including a support having a central axis and a plurality of arms pivotably connected to the support, each arm having a free end and a pair of side edges, the plurality of arms being in a first orientation with the side edges of adjacent arms spaced apart from one another; and pivoting the plurality of arms from the first orientation to a second orientation in which the side edges of the adjacent arms contact one another, the pivoting step compressing the prosthetic heart valve from the expanded condition to a collapsed condition; and/or each arm may be connected to the support by a living hinge; and/or the pivoting step may include advancing a translating member along the plurality of arms from an initial position relatively close to the support to a final position relatively distant from the support; and/or the advancing step may include rotating the translating member relative to the compression member; and/or the prosthetic heart valve may include a stent and an outer cuff, the stent including a plurality of struts, and the pivoting step may push the outer cuff between the struts to an interior of the stent at predetermined locations.

In another embodiment hereof, the prosthetic heart valve may include a stent having struts. A method of collapsing a prosthetic heart valve according to this embodiment includes inserting a separation tool into an opening of a loading base, the separation tool including a shaft having a plurality of ribs extending along a length of the shaft and projecting radially outward from the shaft, adjacent ribs defining channels sized to receive selected ones of the struts; inserting the prosthetic heart valve into the opening; and collapsing the prosthetic heart valve so that the selected ones of the struts of the stent are received within respective ones of the channels of the separation tool and separated from one another by the ribs; and/or the shaft may have nine ribs; and/or the shaft may have three ribs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for collapsing a prosthetic heart valve, comprising:
a compression member including a support having a central axis and a plurality of arms pivotably connected to the support, each of the arms having an inner surface facing the central axis, a pair of side edges, and a free end, the arms being pivotable between a first orientation in which the side edges of adjacent arms are spaced apart from one another and a second orientation in which the side edges of the adjacent arms contact one another, the inner surfaces of the arms collectively defining a compression surface in the second orientation, the compression surface decreasing uniformly in diameter from a first end adjacent the support to a second end adjacent the free ends of the arms, wherein each of the arms extends a length between the support and the free end of the arm and includes an outer side facing away from the central axis, the outer side including a plurality of grooves oriented transverse to the length and spaced apart from one another along the length of the arm, the plurality of grooves collectively defining a threaded portion; and
a translating member threadedly assembled to the threaded portion of the compression member so that rotation of the translating member relative to the compression member moves the translating member along the arms from an initial position in which the arms are in the first orientation and the translating member is relatively close to the support to a final position in which the arms are in the second orientation and the translating member is relatively distant from the support, movement of the translating member from the initial position to the final position pivoting the arms from the first orientation to the second orientation.

2. The device of claim 1, wherein the free ends of the arms in the second orientation collectively define an aperture.

3. The device of claim 1, wherein the threaded portion extends from the support to a location spaced from the free ends of the arms.

4. The device of claim 1, wherein the outer side of each of the arms includes a rib that tapers in thickness from a small thickness relatively close to the support to a large thickness relatively close to the free end of the arm.

5. The device of claim 1, wherein each arm is connected to the support by a living hinge.

6. A method for collapsing a prosthetic heart valve, comprising:
inserting the prosthetic heart valve in an expanded condition into an opening of a compression member, the compression member including a support having a central axis and a plurality of arms pivotably connected to the support, each arm having a free end and a pair of side edges, the plurality of arms being in a first orientation with the side edges of adjacent arms spaced apart from one another; and
pivoting the plurality of arms from the first orientation to a second orientation in which the side edges of the adjacent arms contact one another by rotatably advancing a translating member along grooves of the plurality of arms from an initial position relatively close to the support to a final position relatively distant from the support, the grooves being on an outer side of the arms facing away from the central axis and oriented transverse to a length of the arm and spaced apart from one another along the length of the arm, the inner surfaces of the arms collectively defining a compression surface in the second orientation, the compression surface decreasing uniformly in diameter from a first end adjacent the support to a second end adjacent the free ends of the arms, and the pivoting step compressing the prosthetic heart valve from the expanded condition to a collapsed condition.

7. The method of claim 6, wherein each arm is connected to the support by a living hinge.

8. The method of claim 6, wherein the prosthetic heart valve includes a stent and an outer cuff, the stent including a plurality of struts, and the pivoting step pushes the outer cuff between the struts to an interior of the stent at predetermined locations.

9. A method of collapsing a prosthetic heart valve including a stent having struts, the method comprising:
inserting a separation tool into an opening of a base of a compression member, the separation tool including a shaft having a plurality of ribs extending along a length of the shaft and projecting radially outward from the shaft, adjacent ribs defining channels sized to receive selected ones of the struts, the separation tool being formed of a rigid material;
inserting the prosthetic heart valve into the compression member; and
collapsing the prosthetic heart valve around the separation tool so that the selected ones of the struts of the stent are received within respective ones of the channels of the separation tool and respective ones of the ribs are interposed between adjacent ones of the struts.

10. The method of claim 9, wherein the shaft has nine ribs.

11. The method of claim 9, wherein the shaft has three ribs.

* * * * *